United States Patent [19]

Oueveau et al.

[11] Patent Number: 4,822,369
[45] Date of Patent: Apr. 18, 1989

[54] BONE JOINT PROSTHESIS

[76] Inventors: Gerard Oueveau, Amik-Farm, Les Boulaies, Le Pin 79140, Cerizay; Jacques Moulin, 43, Avenue Edouard Vaillant, 181 Vierzon, both of France

[21] Appl. No.: 872,539
[22] Filed: Jun. 10, 1986
[51] Int. Cl.⁴ .............................................. A61F 3/34
[52] U.S. Cl. ..................................................... 623/22
[58] Field of Search ..................................... 623/16–23

[56] References Cited

U.S. PATENT DOCUMENTS

| 2,947,308 | 8/1960 | Gorman . | |
| 3,067,740 | 12/1962 | Haboush | 623/22 |
| 3,894,297 | 7/1975 | Mittelmeier et al. | 623/22 |
| 3,996,625 | 12/1976 | Norles | 623/22 |
| 4,263,681 | 4/1981 | Notton | 623/18 |
| 4,366,183 | 12/1982 | Ghommidh et al. | 623/16 |
| 4,380,090 | 4/1983 | Ramos | 623/23 |
| 4,427,501 | 1/1984 | Rogers | 623/16 |

FOREIGN PATENT DOCUMENTS

| 0066092 | 4/1982 | European Pat. Off. | 623/22 |
| 0053794 | 6/1982 | European Pat. Off. | 623/22 |
| 2750648 | 5/1979 | Fed. Rep. of Germany | 623/19 |
| 0152055 | 11/1981 | Fed. Rep. of Germany | 623/18 |
| 1047640 | 12/1953 | France . | |
| 2266491 | 10/1975 | France . | |
| 2289162 | 5/1976 | France . | |
| 2310120 | 12/1976 | France | 623/23 |
| 2395739 | 3/1979 | France | 623/22 |
| 2437200 | 4/1980 | France . | |
| 2126096 | 3/1984 | United Kingdom | 623/22 |
| 2126096A | 3/1984 | United Kingdom . | |

Primary Examiner—Richard J. Apley
Assistant Examiner—David J. Isabella
Attorney, Agent, or Firm—Leydig, Voit & Mayer

[57] ABSTRACT

An improved bone joint prosthesis, particularly a whole hip or shoulder prosthesis, provides long life and prevents dislocation. The cotyle has a resilient, shock absorptive layer sandwiched between inner and outer hemispheric elements. The inner element is coated with a low friction coating which cooperates with the head to provide smooth operation and extended life. Materials which may be used include a high density reticulated polyethylene on the cotyle surface in combination with an alumina head. Particularly good results are obtained using a gold cotyle surface in combination with a highly polished chromium oxide head. A retainer which may be readily fastened to the cotyle during implantation is provided to prevent dislocation of the femoral head from the cotyle. In a preferred embodiment, the lip of the retainer is resilient and permits limited displacement of the head while preventing complete dislocation.

14 Claims, 6 Drawing Sheets

SCALE (FIG. 2b)

BONE JOINT PROSTHESIS

This invention relates to an improved bone joint prosthesis and more particularly to a complete prosthetic hip or shoulder joint which may be surgically implanted in a subject to restore the function of the hip or shoulder joint when the natural joint is sufficiently defective or damaged to require a prosthetic replacement.

Prosthetic hip joint devices which join the leg and the pelvis by means of a stem embedded in the femur, a spherical bulb (known as a femoral head) attached to the stem, and a cotyle which is embedded in the pelvis, and which has a hollow spherical socket to receive the femoral head, are well-known. Many known prosthetic devices, however, are susceptible to loosening of the cotle and/or the stem, dislocation of the head from the cotyle and/or rapid deterioration. These undesirable results can delay the recovery of the operative subject and cause numerous secondary effects, including loss of mobility, reduced capacity for employment, a period of extended medical and rehabilitative care, illnesses and infirmities which propagate through the skeletal, respiratory, and cardiovascular systems, and the likelihood of additional surgical replacements. As a consequence, the subject often suffers not only from the replacement of his hip joint and the corresponding postoperative care, which may last up to six months, but also from the defects of an inadequate prosthetic device, which may last throughout the life of the joint, frequently between ten and fifteen years. Replacement of a shoulder joint using known prosthetic devices may result in many of the same or similar problems.

It is therefore an object of the present invention to provide an improved whole hip or shoulder prosthetic device which resists loosening and dislocation and provides durability.

A more specific object of the present invention is to provide a whole hip or shoulder prosthetic device having a force-absorptive cotyle with a smooth yet durable surface which contacts the head.

A further object of the present invention is to provide a whole hip prosthetic device which includes a retainer to prevent dislocation of the prosthetic joint.

Other objects and advantages of this novel prosthetic device will become apparent from the following description and drawings, wherein.

Figure 1:
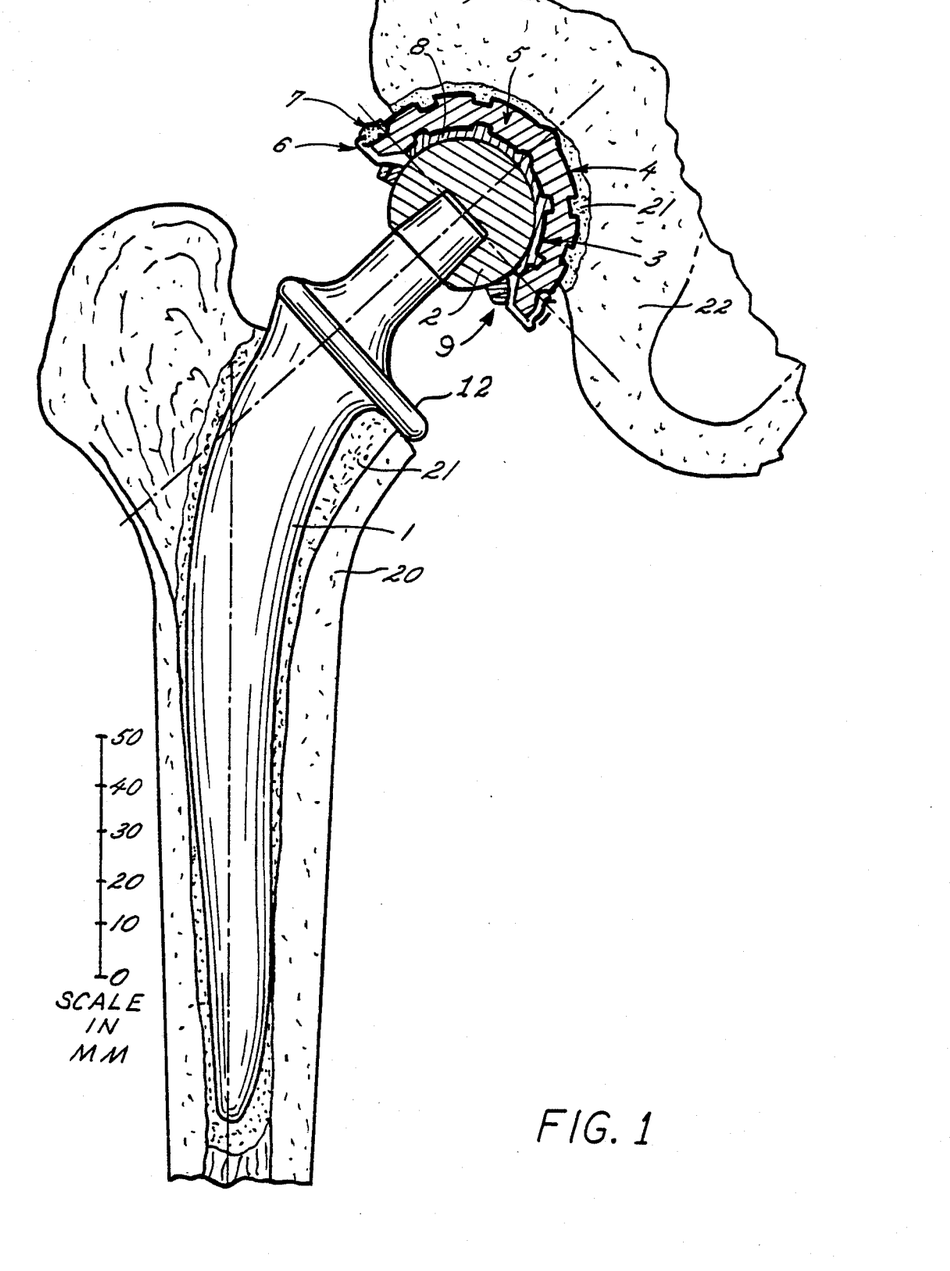
FIG. 1 is a cross-sectional view of a whole hip prosthetic device according to the present invention as embedded in the femur and the pelvis.

Turning now to a detailed description of the various embodiments, FIG. 1 represents a whole hip prosthesis device according to the present invention as it would appear after being surgically implanted in the subject. The actual dimensions of the prosthesis will, of course, vary according to the age and morphology of the subject, and are by no means limited by the dimensional scale, that is provided on the various figures for reference only. A shaft 1 is made preferably of some metallic material and is shaped to conform to the inner cavity of the femur 20. A material which has been found to be particularly suitable is a titanium alloy, $TiAl_6V_4$, though those skilled in the art will recognize that other materials may also be suitable. Preferably the surface of the shaft 1 should have a degree of surface coarseness to provide a more durable connection between the adhesive material 21 and the shaft 1 without risking damage to the femur during any subsequent removal of the shaft. It has been found that a peak to valley surface coarseness of approximately 0.1 to 0.4 mm, as obtained, for example, by shot blasting, yields good results. The shaft 1 is shown with a shoulder 12 which rests upon and is supported by the surface of the femur, which must be surgically prepared to accept and to conform to the prosthetic device.

The femoral head 2 may be attached by various means to the protruding end of the shaft 1. In the embodiment illustrated in FIG. 1, a Morse cone arrangement is shown. With such an arrangement the head may be bonded to the stem, as with an adhesive, either during initial fabrication or at the time of implantation. In order to provide maximum articulation of the femur with the prosthesis of the invention, the surface of the head should define as large a portion of a sphere as is consistent with a strong and secure attachment of the head to the stem. For example, in FIG. 4, an enlargement of the FIG. 1 embodiment, the spherical angle is about 270° or more.

To provide durability, the femoral head 2 should be made of a hard and an abrasion resistant material such as, for example, aluminum oxide ($Al_2O_3$) or chromium oxides ($CrO$ or $Cr_2O_3$). Preferably, the surface of the femoral head 2 is also finely polished to reduce friction.

Figure 4:
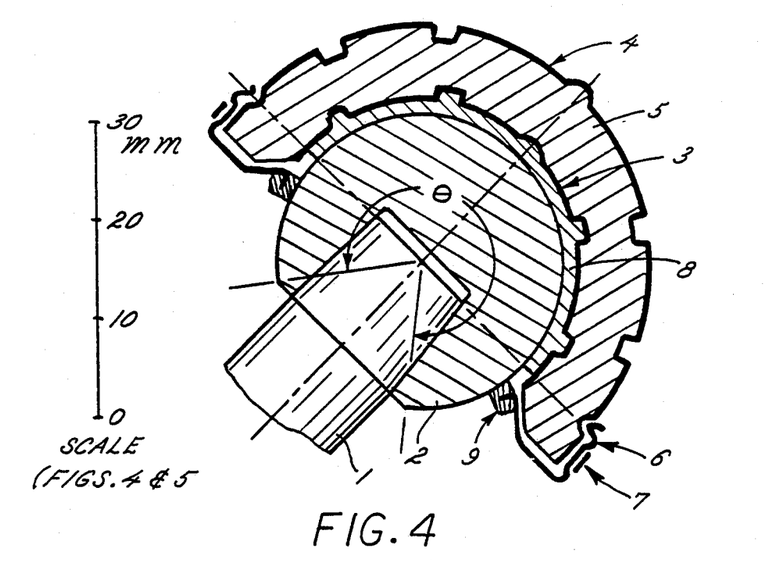
FIG. 4 illustrates an enlarged partial cross-sectional view of the whole hip prosthetic device of FIG. 1.

According to an aspect of the invention illustrated in FIG. 4 the cotyle consists of two substantially concentric, substantially hemispherical shells, an inner shell 3 and an outer shell 4, with a resilient, shock-absorptive material 5 therebetween. This material 5 may be, for example, silicone or polyethylene. As illustrated in the figures, the elastic material is preferably several millimeters in thickness. The presence of the elastic material 5 allows for the even distribution of forces to the outer shell of the cotyle and for the absorption of shocks transmitted into the cotyle from the femoral head by the activity of the subject. This results in increased comfort and reduces the stress on the cohesive joint 21 between the outer surface of the cotyle and the bone structure 22. One suitable fabrication technique is to inject the material 5 under pressure between the shells 3 and 4.

Figure 5:
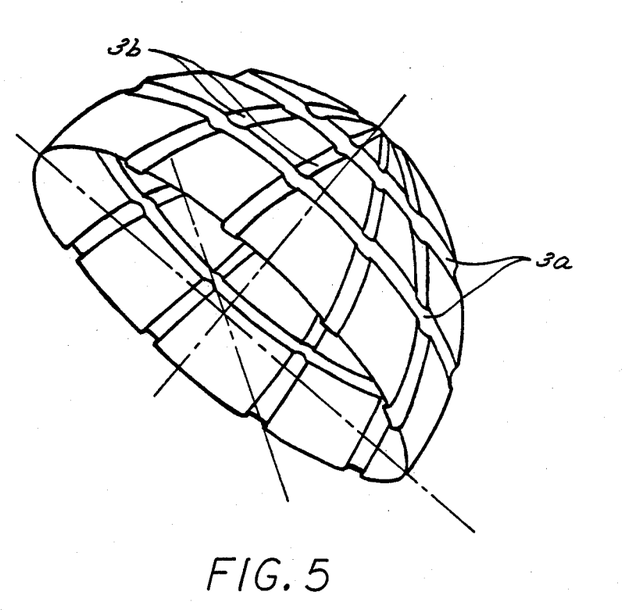
FIG. 5 illustrates a three-dimensional view of the inner shell 3 of the cotyle shown in FIGS. 1 and 4.
Figures 6A, 6B:
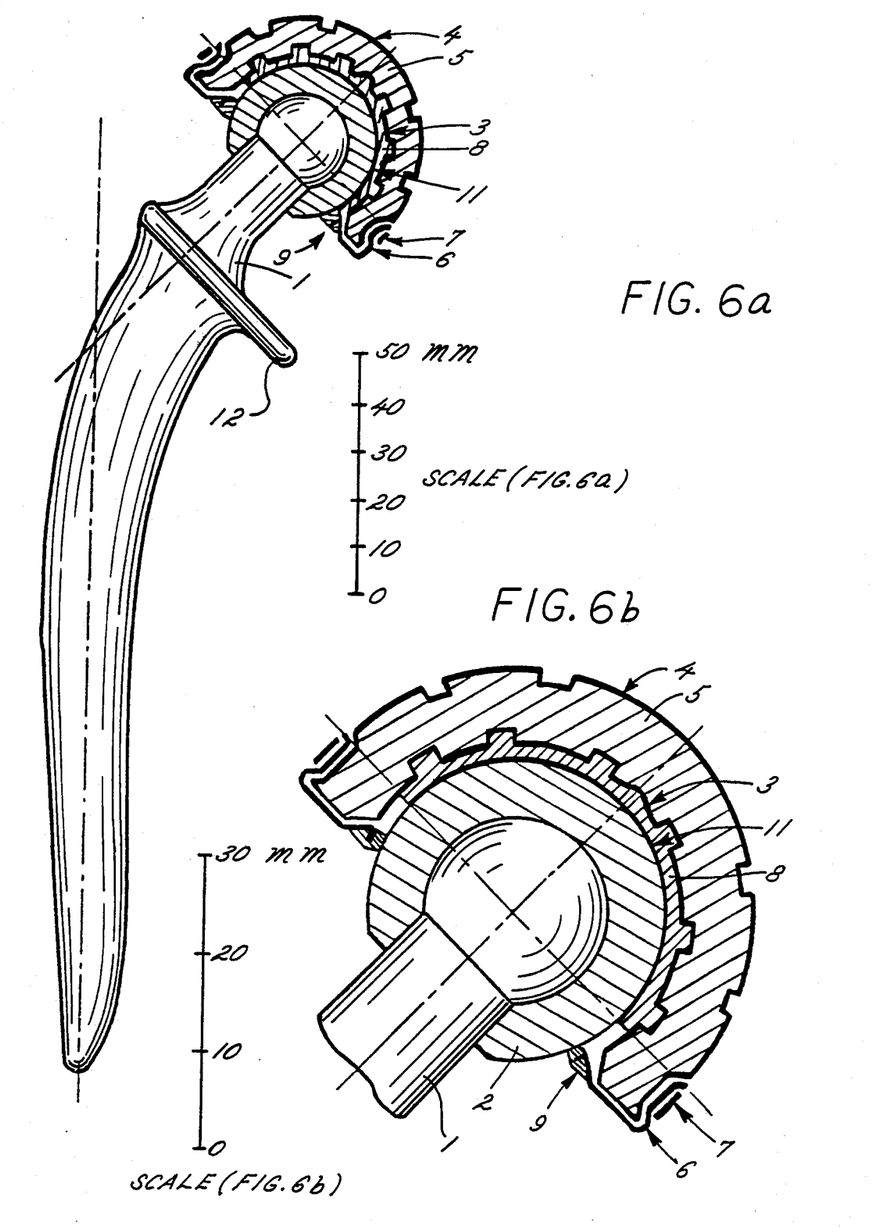
FIGS. 6(a) and 6(b) illustrate another embodiment of a whole hip prosthetic device according to the present invention which includes a modified lip on the retainer 9 and a plated wear surface 11.

It is contemplated that the shells 3 and 4 be made of some durable material, and may vary in thickness and configuration depending upon the specific materials used and the embodiment employed. The inner shell 3 shown is coated on its interior surface with a layer 8 of a low friction material such as, for example, high density reticulated polyethylene or sintered materials such as coated or graphite-impregnated carbides. The inner shell 3 ensures the rigidity of the film 8 and diffuses forces into the elastic material 5, thus reducing motion of the cotyle which could break the cotyle-pelvis seal. FIG. 5 illustrates a shell 3 such as might be used in the FIG. 1 and FIG. 4 embodiment (as well as some of the other embodiments discussed below). The latitudinal and longitudinal ridges shown 3a and 3b, respectively, impart rigidity to the shell 3 and also enhance the bonding between the inner layer 8 and the resilient material 5. Other configurations of ridges or projections may also be employed. The outer shell may also be provided with ridges and/or projections to enhance the bondings to the materials adjacent it. As best illustrated in FIGS. 6a and 6b, the ridges on the shells 3 and 4 may be positioned relative to one another in such a manner as to provide a substantially uniform thickness of the intermediate layer 5. Such an arrangement will provide improved shock absorption and force transmission from the head through the cotyle and ultimately to the pelvis.

Figure 7:
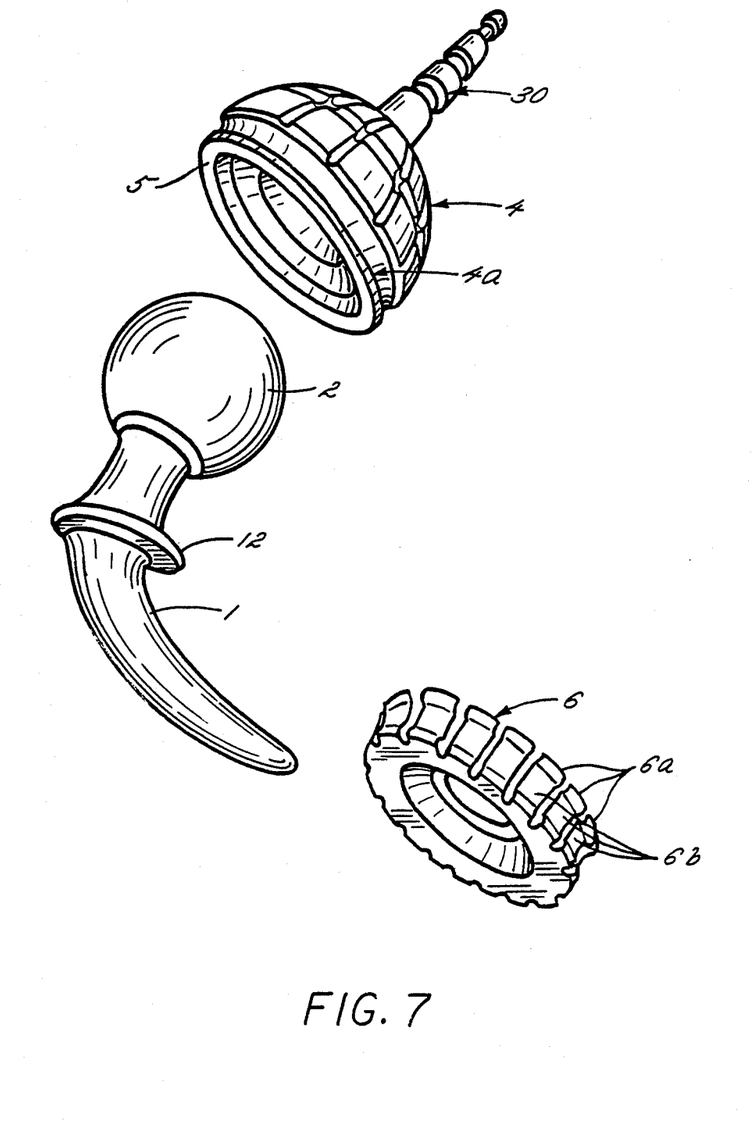
FIG. 7 is an exploded view of an alternative embodiment of the prosthetic device of the present invention as adapted to replace a shoulder joint.

According to another aspect of the invention, a retainer 6, shown in cross-section in FIGS. 1 and 4 (as well as in the other embodiments discussed below) and in perspective in FIG. 7 prevents dislocation of the head from the cotyle. The retainer 6 may be stamped from sheet metal. The titanium alloy noted above, TiAl$_6$V$_4$, is one suitable material. The retainers shown have elements 6a which form a substantially cylindrical recess adapted to receive the circular edge of the substantially hemispherical cotyle, herein called the equatorial edge of the cotyle for reference. As shown in FIG. 7, the elements 6a may be formed with recesses 6b which combine to create a reduced diameter. As also shown in perspective in FIG. 7, the outer surface cotyle may also be formed with an area of reduced diameter 4a spaced from the equatorial edge. With such an arrangement, as shown in FIGS. 2-4 and 6, the retainer may be readily secured in place on the cotyle through the use of a band 7 applied during surgery. Should removal of the retainer ever be required at a later date, it may be accomplished by simply cutting the band 7.

Referring again to FIG. 4, the radially-inner edge of the retainer 6 is provided with a lip element 9 having a diameter less than the maximum diameter of the head 2 such that a dislocation of the head from the hemispherical cavity of the cotyle is prevented. The retainer 6, including the lip element 9, may be coated with the same material as that of the thin film 8 on the inner shell 3. The various embodiments of the prosthesis show variations on the configuration of the retainer 6 and lip element 9.

Figures 2A, 2B:
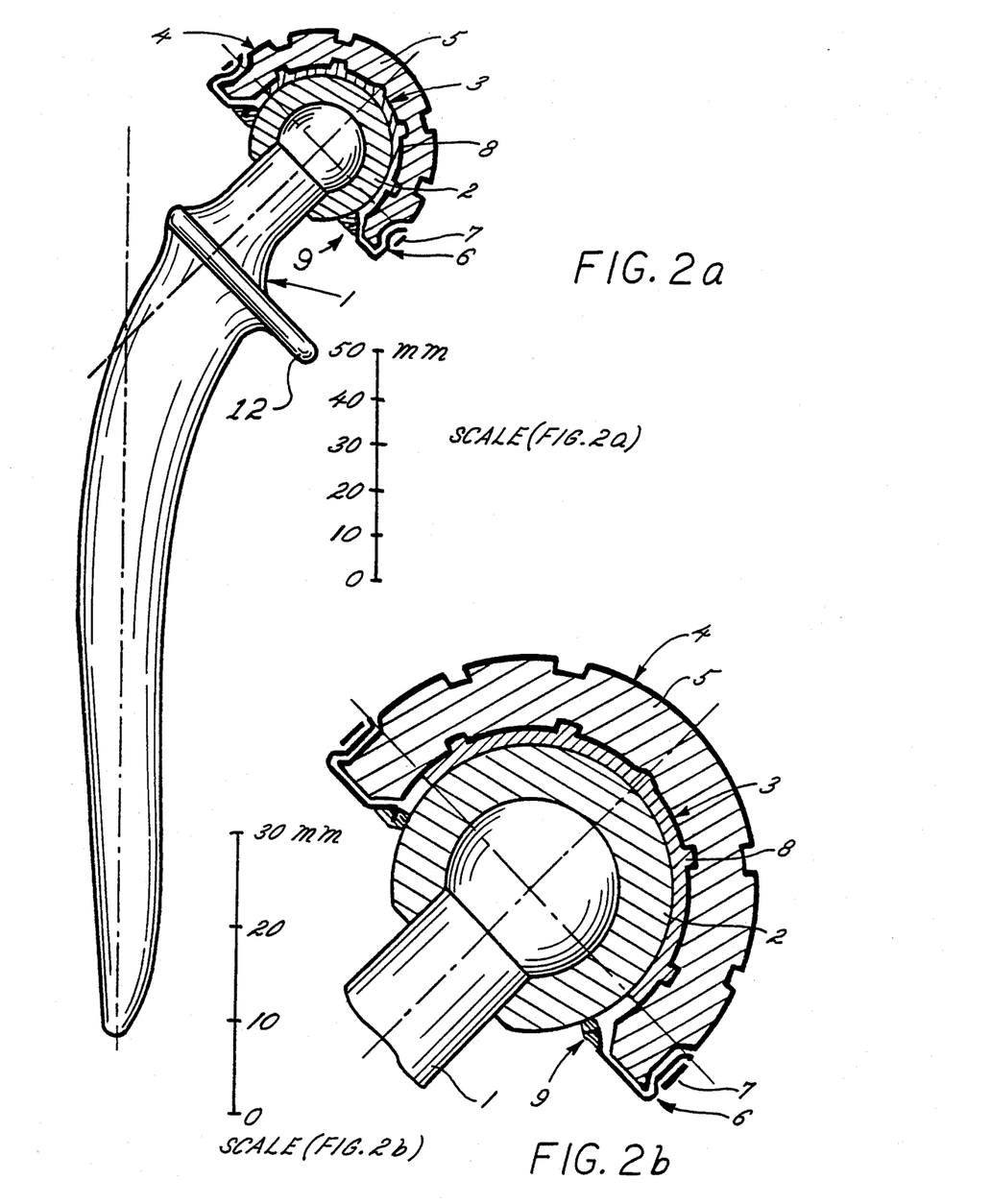
FIGS. 2(a) and 2(b) are an entire cross-sectional view and an enlarged partial cross-sectional view, respectively, of a whole hip prosthetic device according to the present invention having an alternative embodiment of the femoral head.

FIGS. 2a and 2b illustrate an alternate embodiment of the femoral head 2 of the present invention. In this embodiment, the material comprising the femoral head 2 may be sintered directly onto the shaft during fabrication.

Figure 3A:
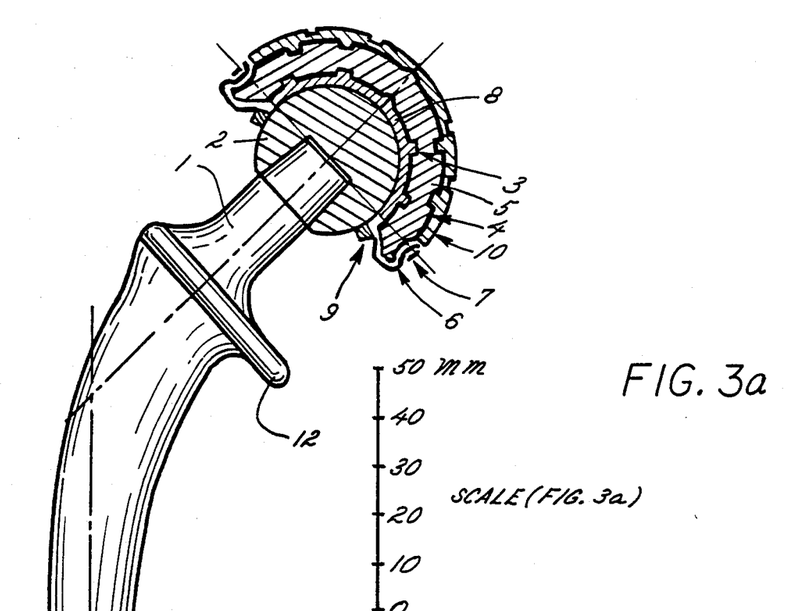
FIGS. 3(a) and 3(b) are figures similar to FIGS. 2a and 2b illustrating a whole hip prosthetic device according to the present invention having a supplemental outer coating on the cotyle.
Figure 3B:
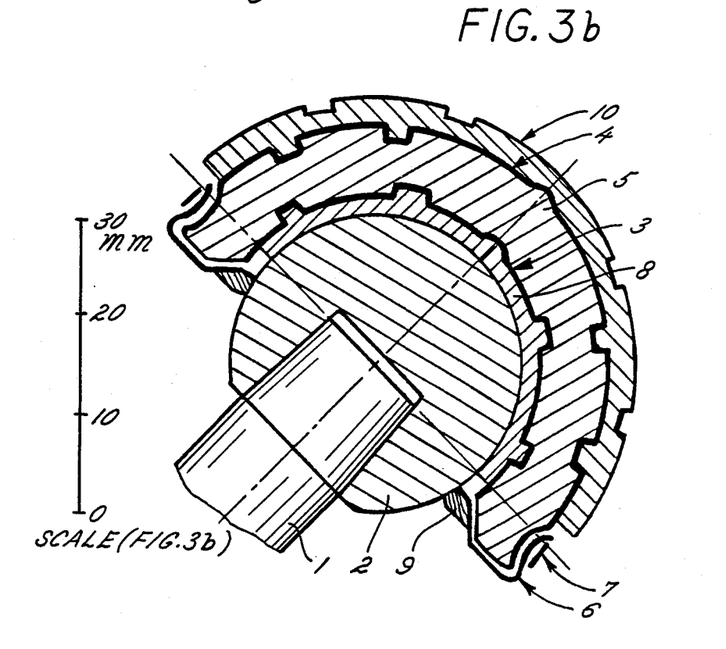

FIG. 3 illustrates an embodiment of the femoral head 2 and cotyle of the present invention in which the outer surface of the outer shell 4 is coated with a material 10 such as high density reticulated polyethylene or a hydroxysphaphetic material such as, for example, calcium phosphate and its derivatives, which favor the colonization of the bone. With such an arrangement, of course, it is the material 10, rather than the shell 4, which is adhered to the pelvis. Such coatings offer an advantage over the FIG. 1 and FIG. 2 embodiments in that the material 10 reinforces the stiffness of the outer shell 4 and promotes good adhesion to the pelvis.

FIG. 6 illustrates another, preferred, embodiment of a whole hip prosthetic device according to the present invention. In this embodiment, the inner shell 3 is thicker and has a smooth, internal contact surface, and is ribbed only on its external surface, which is in contact with the elastic material 5. The titanium alloy noted above, TiAl$_6$V$_4$, has been found to be a particularly suitable material for this embodiment also. It has been found that an internal shell thickness of approximately 2-3 mm yields a rigid shell which is capable of good distribution of forces to the elastic material 5, while still permitting an elastic material thickness of approximately 6 mm.

According to another important aspect of this embodiment, the smooth internal surface of the inner shell 3 is coated with a thin film 11 of gold, which provides very low friction, especially when in contact with a chromium oxide femoral head 2. It has been discovered that an electrolytically-deposited film, a few (e.g., 1 to 3) hundredths of a millimeter thick, is sufficient for this purpose. The combination of gold on the inner hemispherical surface of the shell 3 and polished chromium oxide on the surface of femoral head 2 has been found to provide excellent longevity, even compared with the good combination of high density reticulated polyethylene and aluminum oxide described above. One of the reasons for this is that the ductility of the gold plating permits it to precisely conform to the specific configuration of the head to accommodate manufacturing variations. Such precise conformation avoids areas of high concentrations of forces and wear which might result with a hard surface on both the femoral head and the cotyle.

According to still another aspect of the FIG. 6 embodiment, the lip 9 of the retainer 6 is resilient to allow slight displacement, e.g., 0.5 to 1.0 mm, of the femoral head 2 relative to the cotyle. The resilient lip illustrated may be formed, for example, from polyethylene. By accommodating such displacement, complete dislocation of the head from the cotyle is prevented, while at the same time relieving the bond between the cotyle and the pelvis from much of the stress that would result from more restriction of the head. By permitting the patient's muscles to provide some of the necessary restriction without strain on the cotyle/pelvic bond, the life of the prosthesis can be prolonged. This arrangement also serves to permit the entry of body fluids between the head and the cotyle surface to further reduce friction between the femoral head 2 and the gold film 11.

FIG. 7, which has already been referred to in discussing the retainer 6, illustrates another alternative embodiment of the present invention in which the device is modified to operate as a prosthetic shoulder joint. In this embodiment, a grooved tail 30 is attached to the cotyle to provide additional stability when the device is implanted into the scapula. The features of the various hip prosthesis illustrated in FIGS. 1-6 may be similarly employed in a shoulder prosthesis.

The surgical procedure for implanting the whole hip or shoulder prosthetic device of the present invention conforms to well-known professional surgical practice. In the case of a hip prosthesis, the cotyle is initially mounted on the pelvis. The shaft is then embedded in the femur. The femoral head is inserted into the cavity in the cotyle, and the retainer is mounted to the cotyle at the base of the femoral head, as explained above. A similar procedure would be employed for implantation into a shoulder.

While the specification and illustrations refer to specific structures and materials, it is not intended that the present invention be limited thereto. Changes and variations may be made without departing from the spirit and scope of the invention as defined by the appended claims.

We claim as our invention:

1. A hip or shoulder prosthesis for connecting a thigh bone to a pelvis or a humerus to a scapula comprising a shaft to penetrate the thigh bone or humerus; a substantially spherical head having an outer hemispherical surface with a maximum diameter fastened to the shaft; a cotyle adapted to be fastened to the pelvis or scapula with an adhesive, the cotyle comprising an inner, substantially hemispherical, rigid shell having a substantially hemispherical cavity to receive the head, the cavity having an inner surface being formed of an abrasion resistant, low friction material, an outer, substantially hemispherical rigid shell, the inner shell sized relative to the outer shell to provide a space therebetween, a resilient shock absorption layer between the inner and outer shells and in intimate contact therewith, the resilient shock absorption layer being thicker than the internal and external shells; at least one of the shells having a plurality of ridges formed therein to enhance the rigidity of said shell, each of the ridges being generally convex on one side of the shell and generally concave on the other side of the shell; and a retainer fixed to the cotyle, the retainer comprising a retaining lip having an inside diameter less than the maximum diameter of the head to prevent dislocation of the head from the cotyle cavity.

2. Prosthesis according to claim 1 wherein the surface of the shaft has a peak-to-valley coarseness of between 0.1 mm and 4 mm to provide a secure connection between the haft and the bone cavity into which it is installed.

3. Prosthesis according to claim 1 wherein said horn is fabricated from a titanium alloy.

4. Prosthesis according to claim 1 wherein the inner shell is plated with a smooth layer of gold and the head is fabricated form chromium oxides, the outer hemispherical surface of which is polished.

5. Prosthesis according to claim 1 wherein the head is fabricated from an aluminum oxide.

6. Prosthesis according to claim 1 wherein the head is bonded to the shaft using a Morse cone connection.

7. Prosthesis according to claim 1 wherein the head has a spherical angle of at least 270° with respect to the axis of the end of the shaft which is bonded to the head.

8. Prosthesis according to claim 1 wherein the retaining lip is formed of a resilient material which permits limited displacement of the head within the cotyle while preventing complete dislocation.

9. Prosthesis according to claim 8 wherein the retaining lip is formed from polyethylene, the retaining lip permitting displacement of the head relative to the cotyle of about 0.5 mm to about 1.0 mm.

10. Prosthesis according to claim 1 wherein the outer shell is coated with a material selected from the group of high-density reticulated polyethylene and hydroxysphorphetic materials comprising calcium phosphate and its derivatives.

11. Prosthesis according to claim wherein the inner and outer shells are formed from sheet metal less than about 3 mm thick.

12. Prosthesis according to claim 1 wherein the retainer is formed from sheet metal less than about 3 mm thick.

13. A hip or shoulder prosthesis for connecting a thigh bone to a pelvis or a humerus to a scapula comprising a shaft to penetrate the thigh bone or humerus; a substantially spherical head having an outer hemispherical surface with a maximum diameter fastened to the shafts; a cotyle adapted to be fastened to the pelvis or scapula with an adhesive, the cotyle comprising an inner, substantially hemispherical, rigid shell having a substantially hemispherical cavity to receive the head, the cavity having an inner surface being formed of an abrasion resistant, low friction material, an outer, substantially hemispherical rigid shell, the inner shell sized relative to the outer shell to provide a space therebetween, a resilient shock absorption layer between the inner and outer shells; and a retainer fixed to the cotyle, the retainer comprising a retaining lip having an inside diameter less than the maximum diameter of the head to prevent dislocation of the had from the cotyle cavity and substantially axially projecting elements forming a substantially cylindrical recess, the inside diameter of the recess being adapted to receive the cotyle, the cotyle having an area of reduced diameter at a location spaced from its substantially equatorial edge, the projecting elements of the retainer having mating areas of reduced diameter whereby band means circumscribing the projecting elements at the location of the reduced diameter area will cause the projecting elements to grip the cotyle and prevent dislocation of the head from the cotyle.

14. Prosthesis according to claim 13 wherein the retainer is formed from sheet metal less than about 3 mm thick.

* * * * *

UNITED STATES PATENT AND TRADEMARK OFFICE
CERTIFICATE OF CORRECTION

PATENT NO. : 4,822,369

DATED : April 18, 1989

INVENTOR(S) : Gerard Queveau and Jacques Moulin

It is certified that error appears in the above-identified patent and that said Letters Patent is hereby corrected as shown below:

In the Specification:

Col. 1, l. 17, delete "cotle" and substitute --cotyle--

Col. 2, l. 59, delete "cohesive" and substitute --adhesive--

In the Claims:

Claim 2, col. 5, l. 43, delete "haft" and substitute --shaft--

Claim 3, col. 5, l. 45, delete "said" and substitute --the--

Claim 10, col. 6, ll. 14-15, delete "hydroxysphorphetic" and substitute --hydroxysphophetic--

Claim 11, col. 6, l. 17, insert --1-- after the word "claim"

Claim 13, col. 6, l. 28, delete "shafts" and substitute --shaft--

UNITED STATES PATENT AND TRADEMARK OFFICE
CERTIFICATE OF CORRECTION

PATENT NO. : 4,822,369

DATED : April 18, 1989

INVENTOR(S) : Gerard Queveau and Jacques Moulin

It is certified that error appears in the above-identified patent and that said Letters Patent is hereby corrected as shown below:

Claim 13, col. 6, line 40, delete "had" and substitute --head--

Signed and Sealed this

Twenty-first Day of August, 1990

Attest:

HARRY F. MANBECK, JR.

*Attesting Officer*  *Commissioner of Patents and Trademarks*